US00PP26886P2

(12) United States Plant Patent

Sato et al.

(10) Patent No.: US PP26,886 P2
(45) Date of Patent: Jun. 28, 2016

(54) **NEW GUINEA *IMPATIENS* PLANT NAMED 'SAKIMP036'**

(50) Latin Name: ***Impatiens* hybrid hort**
Varietal Denomination: SAKIMP036

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/544,467

(22) Filed: Jan. 8, 2015

(51) Int. Cl.
*A01H 5/02* (2006.01)

(52) U.S. Cl.
USPC ..... Plt./318.2

(58) Field of Classification Search
USPC ..... Plt./318.1, 318.2
See application file for complete search history.

(56) References Cited

PUBLICATIONS

Sakata Ornamentals 2014 Catalog website (http://www.sakataornamentals.com/_ccLib/attachments/pages/Sakata+Ornamental+Catalog+2014.pdf). Dec. 8, 2015 (2 pages).*
Sakata website (http://sakataornamentals.com/index.cfm/fuseaction/plants.printDetail/plant_ID/3316/index.htm). Dec. 8, 2015 (1 page).*

* cited by examiner

*Primary Examiner* — Susan McCormick Ewoldt
*Assistant Examiner* — Karen Redden
(74) *Attorney, Agent, or Firm* — Barbara Campbell; Bethany R. Roahrig; Cochran Freund & Young, LLC

(57) ABSTRACT

An *impatiens* plant particularly distinguished by having beautiful white flowers with a white eye, a strong root system, and spreading habit, is disclosed.

2 Drawing Sheets

Genus and species: *Impatiens* hybrid hort.
Variety denomination: 'SAKIMP036'.

BACKGROUND OF THE NEW PLANT

The present invention comprises a new and distinct variety of New Guinea *impatiens* plant, botanically known as *Impatiens hybrida* hort, and referred to by the variety name 'SAKIMP036' and characterized by having a clear white color, a strong root system, and a spreading habit. *Impatiens* variety 'SAKIMP036' originated from a hybridization in Misato, Japan in December 2010. The female parent was a proprietary *impatiens* breeding line named 'NE-4391' (unpatented) having blush colored flowers. The male parent was a proprietary impatiens breeding line named 'NJ-302-2H' (unpatented) having white colored flowers and a compact habit.

'SAKIMP036' was selected in December 2010 from the $F_1$ pogeny. From May through August of 2012, 'SAKIMP036' was evaluated for its performance. In May through August 2012, 'SAKIMP036' was first vegetatively propagated, cultivated, and transplanted to the greenhouse and to the field for outdoor evaluation. 'SAKIMP036' was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. White flowers;
2. A strong root system; and
3. A spreading habit.

DESCRIPTION OF THE PHOTOGRAPHS

This *impatiens* plant is illustrated by the accompanying photographs which show the plant's overall plant habit including form, foliage, and flowers. The photographs are of a 4 month old plant grown in Salinas, Calif. under greenhouse conditions in the spring of 2014. The colors shown are as true as can be reasonably obtained by conventional photographic procedures.

DESCRIPTION OF THE NEW VARIETY

Figure 1:
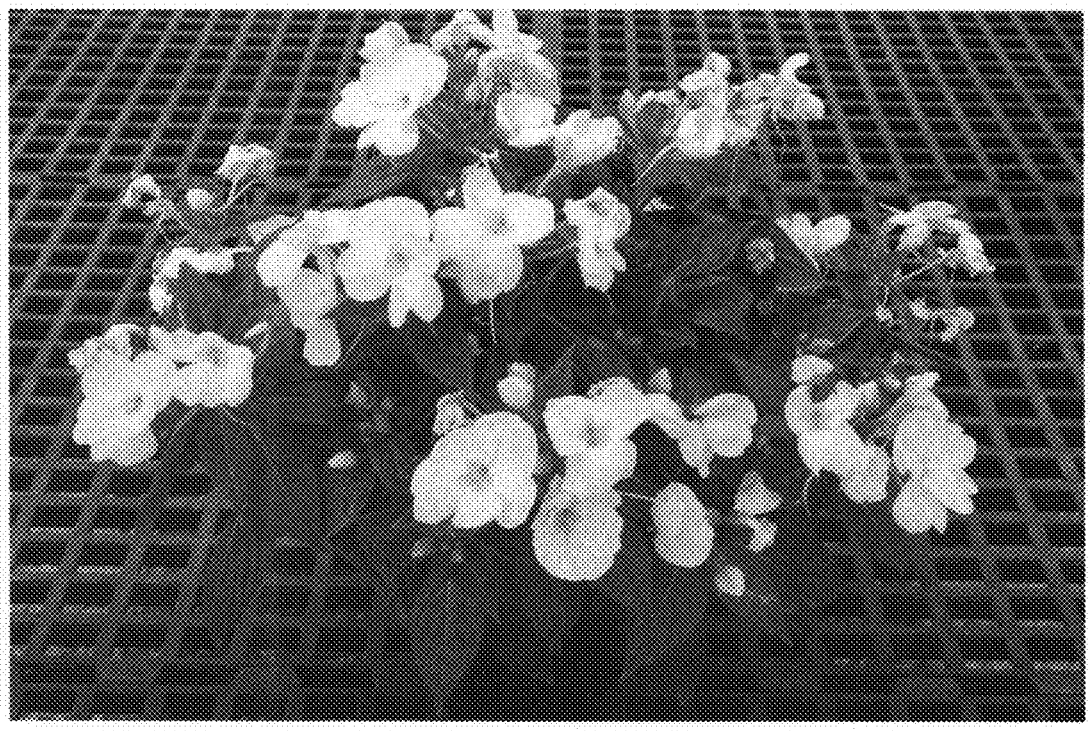
FIG. 1 shows the overall plant habit of the plant grown in a pot.
Figure 2:
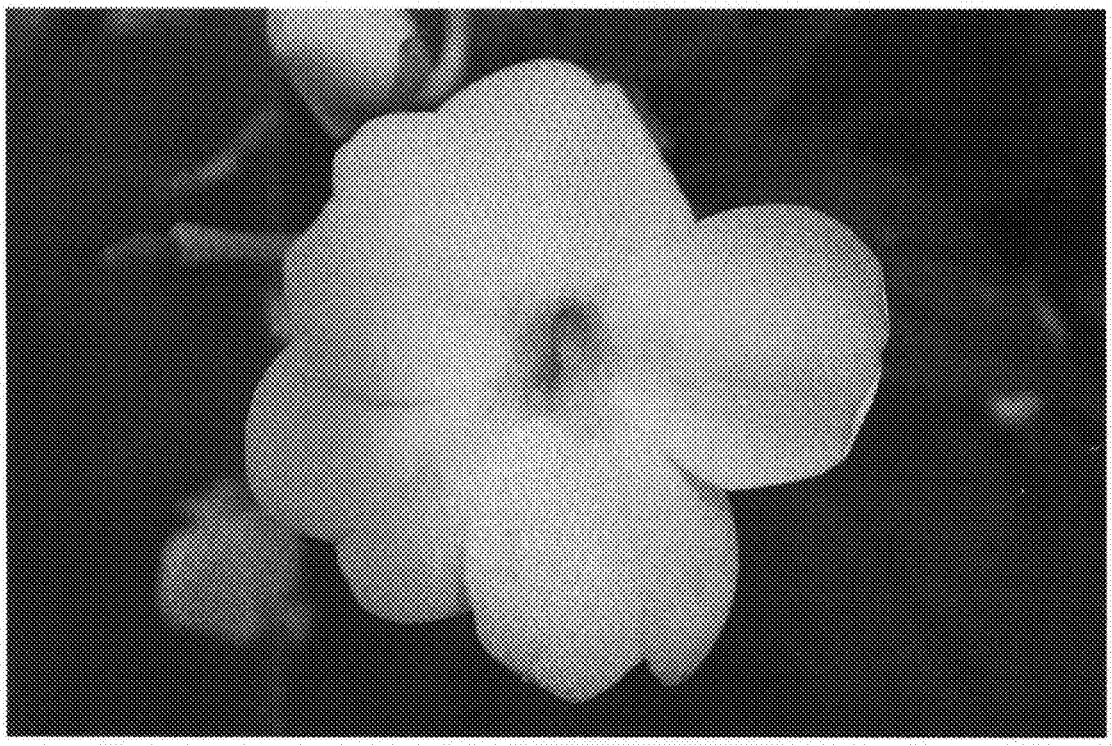
FIG. 2 shows a close-up of the mature inflorescence of the plant.

The following detailed descriptions set forth the distinctive characteristics of 'SAKIMP036'. Data was collected on plants grown three months from transplant into 4-inch posts from rooted cuttings in Salinas, Calif., under greenhouse conditions in the spring 2014. Plants were pinched once during growth. Color references are to The Royal Horticultural Society of London Colour chart (R.H.S.), $4^{th}$ edition (2001). Anatomic labels are from *The Cambridge Illustrated Glossary of Botanical Terms,* by M. Hickey and C. King, Cambridge University Press.

Classification:

*Family*.—Balsaminaceae.
*Botanical*.—*Impatiens hybrida* hort.
*Common*.—*Impatiens*.
*Designation*.—'SAKIMP036'.

Parentage:
*Female parent*.—'NE-4391' (unpatented).
*Male parent*.—'NJ-302-2H' (unpatented).

Growth:
*Time to produce a rooted cutting*.—About 4 weeks.
*Environmental conditions for plant growth*.—The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:
*Habit and form*.—Spreading.
*Height*.—24.0 cm; 1.0 cm from soil line to first node, 3.0 cm from first node to second node.
*Spread*.—46.0 cm.
*Number of branches*.—3 main, 9 total.
*Length of branches*.—7.0 cm.
*Diameter of branches*.—1.5 cm.
*Life cycle*.—Annual.
*Time to bloom from propagation*.—6 to 8 weeks.
*Flowering requirements* (*season*).—Spring to first frost.
*Temperature tolerances*.—Heat tolerant.

Stems:
*Stem color*.—RHS 144A (Yellow-Green) with slight RHS 59C (Red-Purple).
*Anthocyanin color*.—Slight RHS 59C (Red-Purple).
*Stem pubescence*.—Absent.
*Stem description*.—Smooth; circular cross-section.
*Stem length*.—12.0 cm.
*Stem diameter*.—0.7 cm.
*Internode length*.—5.0 cm.

Branches:
*Branch color*.—RHS 144A (Yellow-Green) with RHS 59C (Red-Purple).
*Anthocyanin color*.—RHS 59C (Red-Purple).
*Branch pubescence*.—Absent.
*Branch description*.—Smooth; circular cross-section.
*Branch length*.—7.0 cm.
*Branch diameter*.—1.5 cm.
*Internode length*.—3.0 cm.

Leaves:
*Leaf arrangement*.—Whorled with up to 5 leaves per node; opposite if only 2 leaves at first node.
*Leaf shape*.—Lanceolate; curled.
*Leaf apex*.—Accuminate.
*Leaf base*.—Attenuate.
*Leaf margin*.—Ciliate.
*Leaf surface*.—Dull, waxy.
*Leaf length*.—10.0 cm.
*Leaf width*.—4.5 cm.
*Leaf color*.—Upper: RHS 139A (Green). Lower: RHS 147B (Yellow-Green).
*Leaf variegation*.—Absent.
*Leaf fragrance*.—Absent.
*Leaf surface pubescence*.—Absent.
*Petiole length*.—3.0 cm.
*Petiole diameter*.—4.0 mm.
*Petiole color*.—RHS 145C (Yellow-Green).
*Venation*.—Pinnate.
*Venation color* (*both surfaces*).—RHS 145C (Yellow-Green).

Inflorescence:
*Number of flowers per plant*.—Approximately 60 in bloom.
*Number of flowers per node*.—1 to 3 in bloom; about 4 to 6 flower buds per node.
*Inflorescence type*.—Single flowers with spur; 5 petals.
*Fragrance*.—Absent.
*Lastingness of individual blooms on plant*.—14 days.

Corolla:
*Corolla shape*.—Roughly circular with 5 radial petals.
*Corolla diameter*.—6.0 cm.
*Corolla depth*.—1.0 cm.

Calyx:
*Sepal number*.—2.
*Sepal shape*.—Lanceolate, curled.
*Sepal apex*.—Caudate.
*Sepal base*.—Subcordate.
*Sepal margin*.—Entire.
*Sepal length*.—1.5 cm.
*Sepal width*.—0.8 cm.
*Sepal color* (*both surfaces*).—RHS 145C (Yellow-Green).
*Sepal texture*.—Glabrous.

Bud:
*Bud surface*.—Smooth, shiny, glabrous.
*Bud length*.—1.5 cm.
*Bud diameter*.—1.3 cm.
*Bud shape*.—Deltoid, longitudinal cross-section.
*Bud color*.—RHS 145B (Yellow-Green) with RHS 145A (Yellow-Green) at the edge.

Peduncle:
*Peduncle length*.—4.0 cm.
*Peduncle diameter*.—2.0 mm.
*Peduncle color*.—RHS 145C (Yellow-Green).

Petals:
*Petal pubescence* (*both surfaces*).—Absent.
*Petal length*.—3.0 cm.
*Petal width*.—3.0 cm.
*Petal shape*.—Obcordate.
*Petal apex*.—Emarginate, cleaved.
*Petal margin*.—Entire.
*Petal color* (*both surfaces and eye zone*).—RHS N155A (White).

Spur:
*Spur color*.—RHS 145D (Yellow-Green).
*Spur shape*.—Tubular, curved downward.
*Spur length*.—5.0 cm.
*Spur diameter*.—2.0 mm.

Reproductive organs:
*Stamens*.—Stamen form: Fused, split into 4 lobes. Stamen number: Many. Filament color: RHS N155D (White). Filament length: 0.5 cm. Anther color: RHS N155D (White). Anther length: 1.0 cm.

*Pistil*.—Pistil number: 1. Stigma color: RHS 143A (Green). Style color: RHS 143A (Green). Style length: 0.5 cm.

*Ovary*.—Ovary arrangement: Parietal. Ovary surface color: RHS N144A (Yellow-Green).

*Pollen*.—Pollen amount: Abundant. Pollen description: Powdery. Pollen color: RHS 158A (Yellow-White). Seed production: Absent.

Disease and insect resistance: No particular resistance or susceptibility observed.

COMPARISON WITH PARENTAL LINES AND KNOWN VARIETY

'SAKIMP036' is most similar to the commercial New Guinea *impatiens* variety 'SAKIMP027' (U.S. Plant Pat. No. 24,320); however, there are differences as listed in the table below:

TABLE 1

| Comparison with Similar Variety | | |
|---|---|---|
| Characteristic | 'SAKIMP036' | 'SAKIMP027' |
| Branch color | RHS 144A (Yellow-Green) with RHS 59C (Red-Purple) | Closest to but lighter than RHS 146A (Yellow-Green) |

TABLE 1-continued

| Comparison with Similar Variety | | |
|---|---|---|
| Characteristic | 'SAKIMP036' | 'SAKIMP027' |
| Stem color | RHS 144A (Yellow-Green) with slight RHS 59C (Red-Purple) | RHS 146A (Yellow-Green) |

'SAKIMP036' differs from the parental lines 'NE-439' and 'NJ-302-2H' as described in Table 2 below.

TABLE 2

| Comparison with Parental Lines | | | |
|---|---|---|---|
| Characteristic | 'SAKIMP036' | 'NE-439' | 'NJ-302-2H' |
| Flower color | White | Blush | More white than 'SAKIMP036' |
| Habit | Spreading | | Compact |
| Flower size | Smaller than 'NJ-302-2H' | | Larger than 'SAKIMP036' |

We claim:

1. A new and distinct variety of New Guinea *impatiens* plant named 'SAKIMP036' as described and illustrated herein.

* * * * *